US010874734B2

(12) United States Patent
Nam et al.

(10) Patent No.: US 10,874,734 B2
(45) Date of Patent: Dec. 29, 2020

(54) VARICELLA ZOSTER VIRUS VACCINE

(71) Applicant: MOGAM INSTITUTE FOR BIOMEDICAL RESEARCH, Yongin-si (KR)

(72) Inventors: Hyo Jung Nam, Yongin-si (KR); Eunmi Kim, Yongin-si (KR); Gayoung Ji, Yongin-si (KR)

(73) Assignee: MOGAM INSTITUTE FOR BIOMEDICAL RESEARCH, Gyeonggi-do (KR)

(*) Notice: Subject to any disclaimer, the term of this patent is extended or adjusted under 35 U.S.C. 154(b) by 0 days.

(21) Appl. No.: 16/463,176

(22) PCT Filed: Nov. 24, 2017

(86) PCT No.: PCT/KR2017/013511
§ 371 (c)(1),
(2) Date: May 22, 2019

(87) PCT Pub. No.: WO2018/097642
PCT Pub. Date: May 31, 2018

(65) Prior Publication Data
US 2019/0365884 A1 Dec. 5, 2019

(30) Foreign Application Priority Data

Nov. 25, 2016 (KR) .................. 10-2016-0158243
Nov. 24, 2017 (KR) .................. 10-2017-0158316

(51) Int. Cl.
*A61K 39/25* (2006.01)
*A61K 39/00* (2006.01)

(52) U.S. Cl.
CPC .... *A61K 39/25* (2013.01); *A61K 2039/55505* (2013.01); *C12N 2710/16734* (2013.01); *C12N 2710/16771* (2013.01)

(58) Field of Classification Search
CPC ........ A61K 39/12; A61K 39/25; A61K 39/39; A61K 2039/55505; A61K 2039/545; A61K 39/00; C12N 2710/16734; C12N 2710/16711; C12N 2710/16722; C12N 2710/16771; C07K 14/005; A61P 31/20
See application file for complete search history.

(56) References Cited

U.S. PATENT DOCUMENTS

| 2006/0121052 | A1 | 6/2006 | Sotelo-Morales et al. |
| 2008/0171688 | A1 | 7/2008 | Sotelo-Morales et al. |
| 2008/0226672 | A1 | 9/2008 | Garcon |
| 2010/0310602 | A1* | 12/2010 | Reed ............ A61P 37/00 424/207.1 |
| 2011/0104260 | A1* | 5/2011 | Hanon ............ A61P 31/22 424/450 |

FOREIGN PATENT DOCUMENTS

| KR | 1020140006115 A | 1/2014 |
| KR | 1020150076772 A | 7/2015 |
| WO | 0043527 A1 | 7/2000 |
| WO | 2006094756 A2 | 9/2006 |
| WO | 2006128026 A2 | 11/2006 |
| WO | 2009012486 A1 | 1/2009 |
| WO | 2012115474 A2 | 8/2012 |

OTHER PUBLICATIONS

Dendouga N, Fochesato M, Lockman L, Mossman S, Giannini SL. Cell-mediated immune responses to a varicella-zoster virus glycoprotein E vaccine using both a TLR agonist and QS21 in mice. Vaccine. Apr. 26, 2012;30(20):3126-35. Epub Feb. 10, 2012.*

Clapp T, Siebert P, Chen D, Jones Braun L. Vaccines with aluminum-containing adjuvants: optimizing vaccine efficacy and thermal stability. J Pharm Sci. Feb. 2011;100(2):388-401. Epub Aug. 25, 2010.*

Haumont M, Jacquet A, Massaer M, Deleersnyder V, Mazzu P, Bollen A, Jacobs P. Purification, characterization and immunogenicity of recombinant varicella-zoster virus glycoprotein gE secreted by Chinese hamster ovary cells. Virus Res. Feb. 1996;40(2):199-204.*

Garçon N, Di Pasquale A. From discovery to licensure, the Adjuvant System story. Hum Vaccin Immunother. Jan. 2, 2017;13(1):19-33. Epub Sep. 16, 2016.*

Lee, Na-Kyung, "Adjuvants as Vaccine-Based Technology," Molecular and Cellular Biology Newsletter, 2015 (5 pages, Korean; 12 pages English translation).

Weinberg, Adriana et al., "Varicella-Zoster Virus—Specific Immune Responses to Herpes Zoster in Elderly Participants in a Trial of a Clinically Effective Zoster Vaccine", J Infectious Diseases, 2009, 200(7):1068-1077.

Fradkin, Amber Haynes et al., "Glass Particles as an Adjuvant: A Model for Adverse Immunogenicity of Therapeutic Proteins", J Pharm Sci, 2011, 100(11):4953-4964.

Haumont, M. et al., "Purification, Characterization and Immunogenicity of Recombinant Varicella-zoster Virus Glycoprotein gE Secreted by Chinese Hamster Ovary Cells", Virus Research 1996, vol. 40, pp. 199-204.

International Search Report for International Application No. PCT/KR2017/013511, International Filing Date Nov. 24, 2017, dated Mar. 2, 2018, 10 pages.

Warren-Gash, Charlotte et al., "Varicella and herpes zoster vaccine development: lessons learned", Expert Review of Vaccines, 2017, 16(12): 1191-1201,DOI:10.1080/14760584.2017.1394843.

(Continued)

*Primary Examiner* — Rachel B Gill
(74) *Attorney, Agent, or Firm* — Cantor Colburn LLP

(57) ABSTRACT

The present invention relates to a vaccine composition for prevention or treatment of chicken pox or herpes zoster, the vaccine composition comprising a surface protein (gE) of Varicella Zoster Virus and especially an aluminum salt as an adjuvant. The vaccine composition according to the present invention employs a protein antigen, thus showing greater outstanding stability than a live vaccine and has an optimized mixture ratio of adjuvants to elicit effective antibody induction, thereby being useful as a vaccine for preventing or treating Varicella Zoster Virus-caused chicken pox or herpes zoster.

6 Claims, 4 Drawing Sheets
Specification includes a Sequence Listing.

(56) References Cited

OTHER PUBLICATIONS

Kool, M et al., "Alum adjuvant boosts adaptive immunity by inducing uric acid and activating inflammatory dendritic cells", J Exp Med, 2008, 205(4):869-882.

NCBI Reference Sequence:NP_040190.1, "Envelope Glycoprotein E[Numan Alphaherpesvirus3]" (Feb. 10, 2015).

Gupta, RK "Aluminum compounds as vaccine adjuvants", Adv Drug Deliv Rev, 1998, 32(3): 155-172.

Vecchi, Simone et al., "Aluminum Adjuvant Dose Guidelines in Vaccine Formulation for Preclinical Evaluations", J Pharm Sci. 101(1): 17-20(2012).

Warren HS et al., "Current Status of Immunological Adjuvants", Annu.Rev.Immunol, 1986, 4:369-388.

Berarducci, B., Ikoma, M., Stamatis, S., Sommer, M., Grose, C., & Arvin, A. M. (2006). Essential Functions of the Unique N-Terminal Region of the Varicella-Zoster Virus Glycoprotein E Ectodomain in Viral Replication and in the Pathogenesis of Skin Infection. Journal of Virology, Oct. 2006, 80(19), 9481-9496. doi:10.1128/jvi.00533-06.

English Translation of Notice of Allowance dated Aug. 23, 2019 for KR Patent Application No. 10-2017-0158316.

Notice of Allowance dated Aug. 23, 2019 for KR Patent Application No. 10-2017-0158316.

Extended European Search Report dated Apr. 17, 2020 for EP Patent Application No. 17873254.1.

* cited by examiner

VARICELLA ZOSTER VIRUS VACCINE

CROSS REFERENCE TO RELATED APPLICATIONS

This application is a National Stage application of International Application No. PCT/KR2017/013511, filed Nov. 24, 2017 which claims priority to KR Application No. 10-2016-0158243, filed Nov. 25, 2016, and to KR Application No. 110-2017-0158316, filed Nov. 24, 2017, each of which is incorporated herein by reference in its entirety.

SEQUENCE LISTING

A Sequence Listing, incorporated herein by reference, is submitted in electronic form as an ASCII text file of size 4.9 KB, created Jun. 29, 2020, and named "8KM1766".

TECHNICAL FIELD

The present invention relates to a vaccine composition comprising a surface protein (gE) of a Varicella zoster virus as an antigen.

BACKGROUND ART

Varicella zoster virus (VZV) is a virus that causes varicella mainly in children and adolescents. VZV is a virus that remains dormant in the ganglion cells of sensory roots and cranial nerves for several years once infected, and is reactivated and causes herpes zoster in adults who lose immunity. Varicella (chickenpox) is highly contagious and induces bullous erythema over the entire body accompanied with fever and listlessness once infected. In most normal children, varicella almost never progresses to a severe stage and ultimately progresses to a self-limiting disease. However, it is known that patients who undergo organ transplantation or chemotherapy often suffer from severe symptoms (Adriana Weinberg et al., *J Infectious Diseases*, 200(7):1068, 2009; Judith Breuer et al., *Expert Review of Vaccines*, 2017, DOI:10.1080/14760584.2017.1394843).

Herpes zoster (Varicella zoster) has initial symptoms of tingling and aching in the whole body, like body aches, severe itching, tingling, burning and stabbing pain. A few days later, blister occurs. The more skin lesions there are, the more painful the infection becomes, and older patients tend to suffer from more severe pain. Herpes zoster causes aftereffects of neurogenic pain even when completely cured. It is known that adults over 60 years old suffer from aftereffects such as insomnia, chronic fatigue, severe pain even upon light contact or friction, and depression, although adults under 40 years old relatively seldom exhibit these symptoms.

Representative vaccines for the prevention of varicella include products such as VARIVAX (Merck & Co, Inc.) and VARILRIX (GlaxoSmithKline Biologicals), which were developed using the Oka strain, an attenuated strain developed in 1970. In Korea, a product such as Suduvax (Green Cross) using the MAV/06 strain developed in 1980 is commercially available. The commercially available live vaccine has an average 80% defense efficacy and thus 20% of vaccinees are infected even after vaccination, and stability problems such as the onset of varicella and herpes zoster due to the live virus contained in the vaccine have been continually pointed out.

ZOSTAVAX (Merck & Co, Inc.), which is a live attenuated vaccine of the Oka strain, has been developed as a preventive vaccine against herpes zoster, and it is licensed and sold in the USA and Korea under the condition that it should be used not for children and adolescents, but for adults over 50 years of age, because of the high amount of virus contained in the vaccine. Recently, a vaccine for adults over 50 years of age composed of a viral surface protein (gE) and an immune enhancer (adjuvant) was developed by GlaxoSmithKline Biologicals, and proved to have preventive efficacy in clinical trials.

The antigens used in the early stage of vaccine development were mainly live attenuated bacteria or dead bacteria, but are now being replaced with protein antigens, the structures and ingredients of which are clearly found due to stability problems. However, protein antigens have a problem of low immunogenicity compared to conventional vaccines.

When an antigen with low immunogenicity is used, when a person with a chronic disease or an elderly person who exhibits an insufficient vaccination effect due to lowered immunity, is vaccinated, or when large amounts of vaccines are needed due to a sudden and widespread epidemic such as influenza, and thus it becomes necessary to conserve antigens, an immune enhancer (adjuvant) may be used in combination with an antigen in order to improve the immune response, increase the cross-reactivity of the vaccine, and thereby improve the protective effect against serotype strains not included in the vaccine (Na-Kyung Lee, Special Session, *Molecular Cell Biology Newsletter*, May, 2015).

Immune enhancers (adjuvants), which have been clinically proven to be stable and efficient and are used in most vaccines currently on the market, are typically aluminum salts such as aluminum hydroxide or aluminum phosphate. Although the action mechanism of aluminum on the immune enhancement response has not been clearly elucidated, it is thought that aluminum functions to continuously activate immune cells because it adsorbs to proteins to increase the stability of protein antigens and allows antigens to be gradually released. It has also been reported that aluminum acts as a danger signal on cells to induce IL-1β secretion (Kool M et al., 205 (4): 869, *J Exp Med*, 2008).

On the other hand, aluminum entails side effects such as erythema, subcutaneous nodules, contact hyperalgesia and granulomatous inflammation. In an attempt to solve these problems, the content thereof is reduced. In addition, disadvantageously, an aluminum-containing vaccine should be refrigerated because it is unsuitable for freeze-drying and it is difficult to control the quality thereof because of variation in production lots during the vaccine production process due to low production quality reproducibility.

Compared with the typical expectation that the immune response is improved by the adsorption of aluminum and an antigen, it has recently come to be known that the amount of the immune enhancer and the effect of the immune response are not always proportional. Also, it has been found at present that, as the amount of aluminum present in the vaccine increases, the immune effect increases to a certain extent, but aluminum has a disadvantage of suppressing immunogenicity, because the use of excess aluminum may completely negate the effects of the antigen or cause a toxic effect on macrophages. Rather, the adsorption of protein antigens and aluminum has recently been shown to increase thermal stability rather than the synergistic effect of the immune response (Amber Haynes Fradkin et al., 100 (11): 4953, *J. Pharm. Sci.*, 2011).

In addition, aluminum does not exert the same immune enhancement effect for all antigens. It has been known that it cannot exert its function as an immune enhancer for typhoid vaccines, influenza haemagglutinin antigens and tetanus toxin-binding influenza b (Hib) capsular polysaccharides (R K Gupta et al., 32(3): 155, *Adv. Drug Deliv. Rev.*, 1998).

Accordingly, as the result of intensive efforts to improve the immunity-inducing ability of Varicella-zoster-virus-derived protein antigens regarding the development of varicella and herpes zoster vaccines containing protein antigens, the present inventors have found that the immunity-inducing ability thereof was remarkably improved when aluminum is used at a certain ratio as an immune enhancer (adjuvant). Based on this finding, the present invention was completed.

The above information disclosed in this Background section is provided only for enhancement of understanding of the background of the invention and therefore it may contain information that does not form the prior art that is already known to a person having ordinary skill in the art.

DISCLOSURE

Technical Problem

Therefore, it is an object of the present invention to provide a vaccine composition for preventing or treating varicella or herpes zoster comprising a surface protein (gE) of Varicella zoster virus and an immune enhancer (adjuvant).

Technical Solution

To achieve the above object, the present invention provides a vaccine composition for preventing or treating varicella or herpes zoster comprising a surface protein (gE) of Varicella zoster virus having an amino acid sequence set forth in SEQ ID NO: 1 and an immune enhancer (adjuvant).

The present invention also provides a method for preventing or treating varicella or herpes zoster using a vaccine composition comprising a surface protein (gE) of Varicella zoster virus having an amino acid sequence set forth in SEQ ID NO: 1 and an immune enhancer (adjuvant).

The present invention also provides a use of a vaccine composition comprising a surface protein (gE) of Varicella zoster virus having an amino acid sequence set forth in SEQ ID NO: 1 and an immune enhancer (adjuvant) for the prevention or treatment of varicella or herpes zoster.

The present invention also provides a vaccine composition for preventing or treating varicella or herpes zoster, wherein a content ratio of a surface protein (gE) of Varicella zoster virus and an aluminum cation ($Al^{3+}$) is 9:1000 to 22:1000 (weight ratio).

The present invention also provides a method for preventing or treating varicella or herpes zoster using a vaccine composition, wherein a content ratio of a surface protein (gE) of Varicella zoster virus and an aluminum cation ($Al^{3+}$) is 9:1000 to 22:1000 (weight ratio).

The present invention also provides a use of a vaccine composition for the prevention or treatment of varicella or herpes zoster, wherein a content ratio of a surface protein (gE) of Varicella zoster virus and an aluminum cation ($Al^{3+}$) is 9:1000 to 22:1000 (weight ratio).

DETAILED DESCRIPTION OF THE INVENTION

Figure 1:
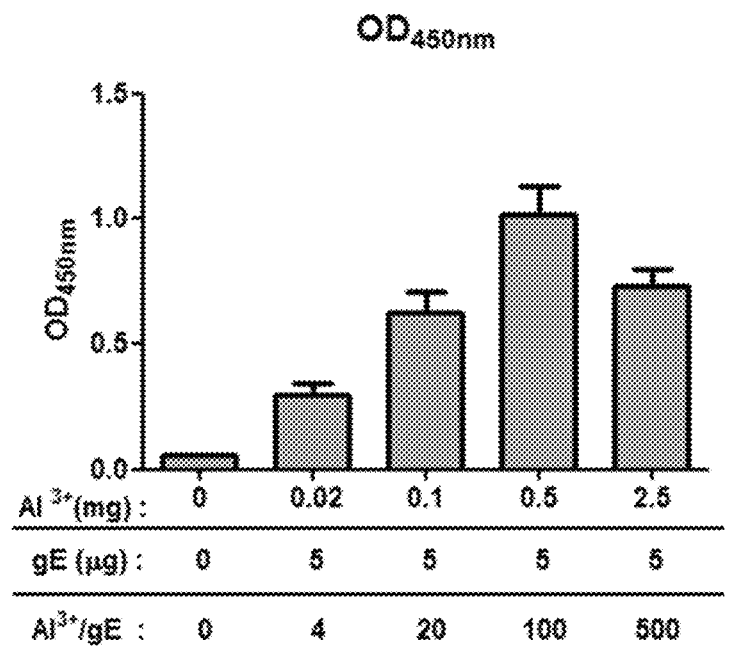
FIG. 1 is a graph showing antibody-inducing ability depending on the concentration of aluminum cation ($Al^{3+}$) relative to 5 μg of a surface protein (gE) of Varicella zoster virus in mice.
Figure 1:
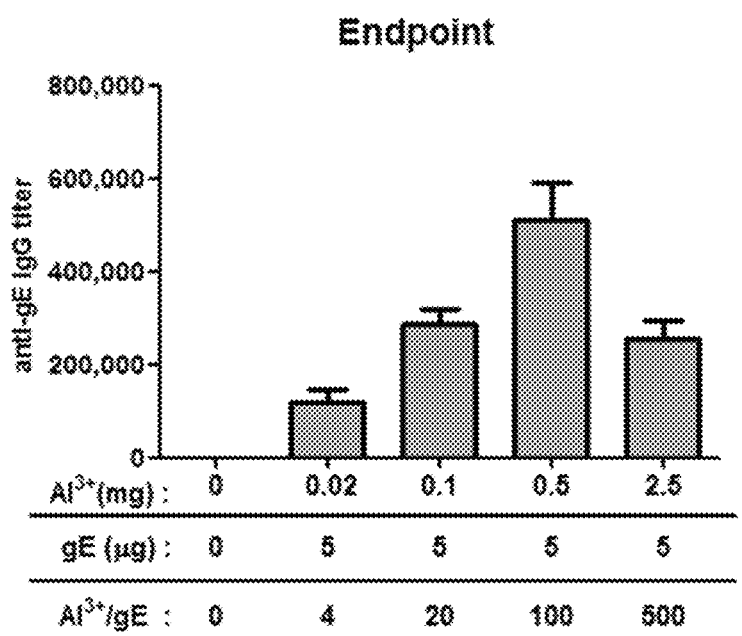

Unless defined otherwise, all technical and scientific terms used herein have the same meanings as appreciated by those skilled in the field to which the present invention pertains. In general, the nomenclature used herein is well-known in the art and is ordinarily used.

According to an embodiment of the present invention, a surface protein (gE) of Varicella zoster virus having an amino acid sequence set forth in SEQ ID NO: 1 as an antigen was mixed with an immune enhancer (adjuvant) to prepare a Varicella Zoster Virus vaccine composition, the vaccine composition was administered to animals, and then antigen-specific immunity was identified.

Accordingly, in one aspect, the present invention is directed to a vaccine composition for preventing or treating varicella or herpes zoster comprising a surface protein (gE) of Varicella zoster virus having an amino acid sequence set forth in SEQ ID NO: 1 and an immune enhancer (adjuvant).

In another aspect, the present invention is directed to a method for preventing or treating varicella or herpes zoster using a vaccine composition comprising a surface protein (gE) of Varicella zoster virus having an amino acid sequence set forth in SEQ ID NO: 1 and an immune enhancer (adjuvant).

In another aspect, the present invention is directed to a use of a vaccine composition comprising a surface protein (gE) of Varicella zoster virus having an amino acid sequence set forth in SEQ ID NO: 1 and an immune enhancer (adjuvant) for the prevention or treatment of varicella or herpes zoster.

The surface protein (gE) of the present invention is derived from a glycoprotein constituting the envelope of Varicella zoster virus derived from Clade 1, and has an amino acid sequence set forth in SEQ ID NO: 1, which is a peptide fragment (truncated protein) composed of 537 amino acids, a part of the c-terminus of which is removed.

When taking into consideration biologically equivalent amino acid variations, the amino acid sequence used in the present invention is interpreted to include a sequence having substantial identity with the sequence of SEQ ID NO: 1. The term "substantial identity" means that a sequence has a homology of at least 70%, more specifically a homology of 80%, even more specifically a homology of 90%, and most particularly a homology of 95%, when aligning the sequence of the present invention with any other sequence so as to correspond to each other as much as possible and analyzing the aligned sequence using algorithms commonly used in the art.

The adjuvant is mixed in order to improve the effect of the vaccine composition, since the surface protein (gE) of Varicella zoster virus according to the present invention is a protein antigen and the protein antigen alone typically induces a weak immune response.

The adjuvant used in the present invention is an aluminum salt, specifically aluminum hydroxide or aluminum phosphate, but is not limited thereto.

As used herein, the term "aluminum" means a trivalent aluminum cation ($Al^{3+}$) itself, excluding an anionic inorganic or organic salt in an aluminum salt. Thus, "the content of aluminum in a composition" means the content of an aluminum cation, not an entire aluminum salt.

The relation between the mass of an aluminum cation and the total mass of a particular type of aluminum salt is well-known in the art. For example, 1 mg of $Al^{3+}$ is present in 2.890 mg of aluminum hydroxide [$Al(OH)_3$]), and 1 mg of $Al^{3+}$ is present in 4.533 mg of aluminum phosphate ($AlPO_4$) [Simone Vecchi et al., *J. Pharm. Sci.* 101 (1): 17-20 (2012)].

In the present invention, the term "immune enhancer" refers to a substance that non-specifically stimulates an immune response to an antigen in the initial process of activating immune cells, such as an agent or molecule which enhances immunity by enhancing the activity of cells of the immune system, although it does not act as an immunogen on a host (Warren et al., *Annu. Rev. Immunol.*, 4: 369, 1986). The immune enhancer that can enhance the immune response used in the present invention may be administered simultaneously with the vaccine composition or may be sequentially administered therewith at a time interval.

In the vaccine composition of the present invention, the content of the surface protein (gE) may be 1 to 125 μg, specifically 1 to 30 μg, and more specifically 5 to 25 μg. Most specifically, the content of the surface protein (gE) may be any one selected from 5, 10, 15, 20 and 25 μg.

In the present invention, the term "prevention" means inhibiting the occurrence of a disorder or a disease in a subject who has never been diagnosed as having the disorder or disease, but is likely to suffer from such disorder or disease.

As used herein, the term "treatment" means (a) inhibiting the progress of a disorder, disease or symptom; (b) alleviating the disorder, disease or symptom; or (c) eliminating the disorder, disease or symptom. The composition of the present invention functions to inhibit the progress of symptoms, or to eliminate or alleviate the progress of symptoms by activating an immune response against Varicella zoster virus in a subject who suffers from varicella or herpes zoster, which is a disease caused by Varicella zoster virus. Thus, the composition of the present invention may serve as a therapeutic composition for varicella or herpes zoster alone, or may be administered in combination with other pharmacological ingredients and applied as a therapeutic aid for the disease.

As herein used, the term "treatment" or "therapeutic agent" encompasses "treatment aid" or "therapeutic aid agent".

The vaccine composition of the present invention may further contain an immune enhancer (adjuvant) consisting of calcium phosphate hydroxide, a mineral oil, squalene, an agonist of a toll-like receptor (TLR), a surfactant (detergent), liposome, saponin, cytokine, or a combination thereof.

As herein used, the term "effective amount" is intended to mean a vaccine composition sufficient to realize the desired effect, which includes, but is not limited to, inducing/increasing an immune response to Varicella zoster virus in a patient, preventing, alleviating or eliminating reactivation of the corresponding virus in a patient infected with Varicella zoster virus or administered with a live vaccine of Varicella zoster virus, preventing herpes zoster (HZ) and/or postherpetic neuralgia (PHN) and reducing the severity or duration of HZ and/or PHN. Those skilled in the art are aware that such a level may vary.

Figure 2:
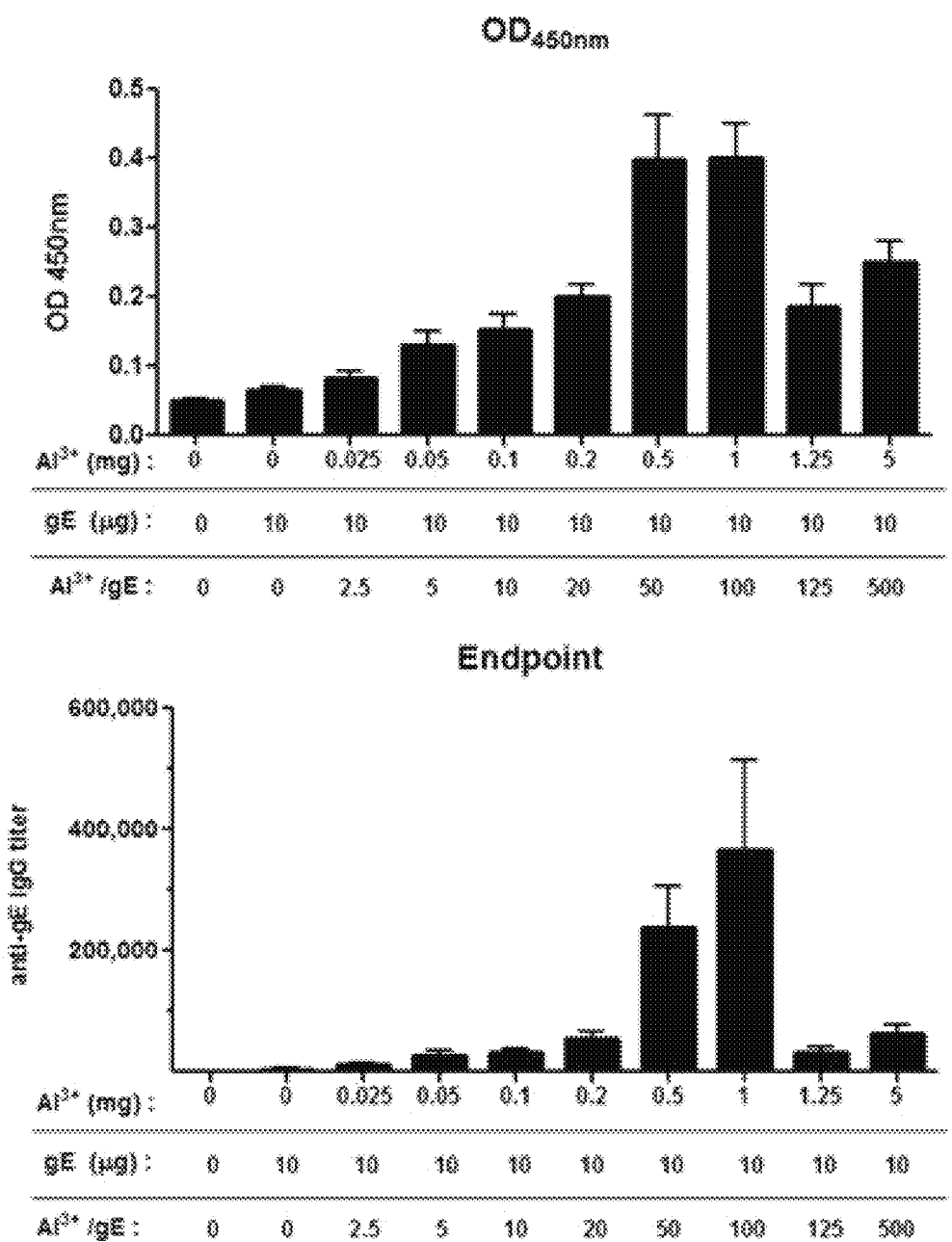
FIG. 2 is a graph showing antibody-inducing ability depending on the concentration of aluminum cations ($Al^{3+}$) relative to 10 μg of a surface protein (gE) in mice.

In one embodiment of the present invention, the optimum content ratio between the above-mentioned surface protein (gE) and the aluminum cation ($Al^{3+}$) is determined by identifying that optimal antibody-forming ability is obtained using 0.5 mg of an aluminum cation ($Al^{3+}$), when the concentration of surface protein (gE) is fixed at 5 μg and the concentration of aluminum is sequentially increased (FIG. 1), and that optimal antibody-forming ability is obtained at 1 mg of an aluminum cation ($Al^{3+}$), when the concentration of the surface protein (gE) is fixed at 10 μg and the amount of aluminum is sequentially increased (FIG. 2).

In particular, the results of the experiments disclosed in FIGS. 1 and 2 according to the present invention are obtained from different animal and immunological schedules, which demonstrate in various aspects that the ratio of antigen (gE) to aluminum cation ($Al^{3+}$) in the vaccine composition according to the present invention is an optimal ratio that can be typically used as a vaccine composition against Varicella zoster virus, regardless of administration conditions.

Thus, in another aspect, the present invention is directed to a vaccine composition for preventing or treating varicella or herpes zoster comprising a surface protein (gE) of Varicella zoster virus and an aluminum salt as active ingredients, wherein a content ratio of the surface protein (gE) to aluminum in the composition is 9:1000 to 22:1000 (weight ratio).

The content ratio of the surface protein (gE) and aluminum in the vaccine composition is specifically 9:1000 to 13:1000 (weight ratio), more specifically 9:1000 to 11:1000 (weight ratio), and most specifically 1:100 (weight ratio).

Or the content ratio of the surface protein (gE) and aluminum in the vaccine composition is specifically 18:1000 to 22:1000 (weight ratio), more specifically 19:1000 to 21:1000 (weight ratio), and most specifically 20:1000 (weight ratio).

In another aspect, the present invention is directed to a method for preventing or treating varicella or herpes zoster using a vaccine composition comprising a surface protein (gE) of Varicella zoster virus and an aluminum salt as active ingredients, wherein a content ratio (weight ratio) of the surface protein (gE) and aluminum in the composition is 9:1000 to 22:1000 (weight ratio).

In another aspect, the present invention is directed to a use of a vaccine composition comprising a surface protein (gE) of Varicella zoster virus and an aluminum salt as active ingredients, for the prevention or treatment of varicella or herpes zoster, wherein a content ratio of the surface protein (gE) and aluminum in the composition is 9:1000 to 22:1000 (weight ratio).

The aluminum salt used in the present invention may specifically be aluminum hydroxide or aluminum phosphate, but is not limited thereto.

In the treatment method and use of the present invention, the content ratio of the surface protein (gE) to the adjuvant is 3:1000 to 30:1000 (weight ratio), specifically 5:1000 to 15:10000 (weight ratio), and more specifically, the content ratio of the surface protein (gE) to the aluminum is 9:1000 to 13:1000 (weight ratio), more specifically 9:1000 to 11:1000 (weight ratio), and most specifically 1:100 (weight ratio).

In the method for the prevention or treatment of varicella or herpes zoster of the present invention and the vaccine composition for use therefor, the content ratio of the surface protein (gE) and aluminum may be 18:1000 to 22:1000 (weight ratio), more specifically 19:1000 to 21:1000 (weight ratio), and most specifically 20:1000 (weight ratio).

The aluminum content is 0.025 to 5 mg, specifically 0.2 to 5 mg, more specifically 0.2 to 1.0 mg, and most specifically 0.5 to 1.0 mg, but is not limited thereto.

The surface protein (gE) of the present invention is derived from a glycoprotein constituting the envelope of Varicella zoster virus derived from Clade 1, and has an amino acid sequence set forth in SEQ ID NO: 1, which is a peptide fragment (truncated protein) composed of 537 amino acids, a part of the c-terminus of which is removed.

In the method for the prevention or treatment of varicella or herpes zoster of the present invention and the vaccine composition for use therefor, the content of the surface protein (gE) may be 1 to 125 μg, specifically 1 to 30 μg, and more specifically 5 to 25 μg. Most specifically, the content of the surface protein (gE) may be any one selected from 5, 10, 15, 20 and 25 μg.

The vaccine composition according to the present invention induces or increases an immune response to Varicella zoster virus in a subject who administers the vaccine composition; prevents, alleviates, eliminates or reduces possibility of reactivation of the virus in a patient infected with the virus, or administered with a live vaccine against the virus; and/or prevents or reduces the possibility of onset of other disease or complications associated with the reactivation of the virus, for example, post-herpetic neuralgia (PHN).

As used herein, the term "immune response" refers to a cell-mediated (T-cell) immune response and/or an antibody (B-cell) response.

The optimal dosage of the vaccine composition of the present invention can be determined through standard studies including observation of immune responses suitable for subjects. After the initial vaccination, the subject may be treated to booster immunization once or several times at appropriate intervals.

The appropriate dosage of the vaccine composition of the present invention may be variably determined based on factors such as formulation method, administration method, and the age, body weight, gender, pathological condition, diet, administration time, administration route, excretion rate and responsiveness of the patient.

The vaccine composition of the present invention may be administered to a patient via a route including, but not limited to, subcutaneous injection, intradermal introduction, imprinting through the skin, or another route of administration, for example, intravenous, intramuscular or inhalation delivery, specifically, subcutaneous or intramuscular administration.

The vaccine composition of the present invention may be useful for preventing varicella and/or HZ and/or PHN, or reducing the severity or duration of varicella, and/or HZ and/or PHN in healthy individuals and immunocompromised patients who have received hematopoietic cell transplantation (HCT) or solid organ transplantation (SOT), HIV-infected patients, patients with autoimmune disease, and individuals with blood cancer; individuals receiving chemotherapy for any of a wide range of solid malignant tumors; and populations of immunocompetent and immunocompromised patients, including, but not limited to, patients undergoing chronic immunosuppressive therapy for any of a wide range of conditions including rheumatoid arthritis (RA), systemic lupus (SLE), Crohn's disease, psoriasis and multiple sclerosis.

The vaccine composition of the present invention may be prepared into a unit dosage form, or may be incorporated into a multi-dose container by formulating the same using a pharmaceutically acceptable carrier and/or excipient according to a method that can be easily carried out by a person having ordinary skill in the art to which the present invention pertains. The formulation may be prepared and used in the form of oral formulations such as powders, granules, tablets, capsules, suspensions, emulsions, syrups and aerosols, and external preparations, suppositories and sterilized injection solutions according to a conventional method. Suitable formulations known in the art may be those disclosed in the document (Remington's Pharmaceutical Science, Mack Publishing Company, Easton Pa.). Solid formulations for oral administration include tablets, pills, powders, granules, capsules and the like. Such solid formulations are prepared by mixing at least one excipient such as starch, calcium carbonate, sucrose, lactose, gelatin and the like. In addition to simple excipients, lubricants such as magnesium stearate and talc are also used. Liquid formulations for oral administration include suspensions, solutions, emulsions, syrups and the like. Various excipients such as wetting agents, sweeteners, fragrances, preservatives and the like may be included, in addition to water and liquid paraffin, which are simple diluents that are commonly used. Formulations for parenteral administration include sterilized aqueous solutions, non-aqueous solutions, suspensions, emulsions, freeze-dried preparations, and suppositories. Examples of the suppository base include Witepsol, macrogol, Tween 61, cacao butter, laurin butter, glycerogelatin and the like.

Hereinafter, the present invention will be described in more detail with reference to examples. However, it will be obvious to those skilled in the art that these examples are suggested only for better understanding of the present invention and should not be construed as limiting the scope of the present invention.

Example 1: Preparation of Protein Antigen (gE)

A fragment (537 aa) of SEQ ID NO: 1 was selected as a fragment capable of most efficiently inducing an immune response among gene fragments encoding the surface protein (gE) of the Varicella zoster virus. A nucleic acid encoding the fragment of SEQ ID NO: 1 was inserted into the expression vector pMSID2 disclosed in Korean Publication No. 2015-0076772 to prepare a pMSID2-MGgE plasmid, CHO (Chinese hamster ovary) cells were transfected with the plasmid, and then a stable cell line expressing gE was produced. The cell line was cultured for 14 days, the culture supernatant was collected, filtered, subjected to anion exchange chromatography and hydrophobic interaction chromatography, subjected to UF/DF, and subjected to nanofiltration and sterilization filtration, to purify the gE protein.

Example 2: Animal Immunization

The following experiment was conducted on mice in order to identify the vaccine efficacy of a composition, which is a mixture of an aluminum salt with the surface protein (gE) of Varicella zoster virus prepared in Example 1 as an antigen.

0.1 ml of a vaccine composition containing a gE antigen and an aluminum salt (aluminum hydroxide, Alhydrogel®, Invivogen) was intramuscularly injected (IM) into the left femur muscle of each group of 5-week-old female C57BL/6 mice (Orient Bio Co., Ltd., Korea), as shown in Table 1. At the 6th week, the mice were sacrificed and 100 μl or more of blood collected from the mice was allowed to stand at room temperature for 20 minutes, and was centrifuged at 5±3° C. and at 10,000 rpm for 10 minutes, serum was obtained as a supernatant. The obtained serum was stored at −15° C. or lower.

TABLE 1

| Group | Composition of vaccine | Dosage (/100 μL) gE | Dosage (/100 μL) Al$^{3+}$ | Number of animals | Day of immunization | Day of bleeding | Day of sacrifice |
|---|---|---|---|---|---|---|---|
| 1 | Negative | X | X | 5 | wk 0 | wk 0 | wk 6 |
| 2 | gE + Alum | 5 μg | 0.02 mg | 5 | wk 3 | wk 3 | |
| 3 | gE + Alum | 5 μg | 0.1 mg | 5 | | wk 6 | |
| 4 | gE + Alum | 5 μg | 0.5 mg | 5 | | | |
| 5 | gE + Alum | 5 μg | 2.5 mg | 5 | | | |
| | Total | | | | | | |

In order to identify the content ratios depending on conditions based on differences in terms of immunization and animals, a surface protein (gE) and an aluminum salt (aluminum hydroxide, Alhydrogel®, Invivogen) were mixed at each ratio shown in Table 2, the mixture was intramuscularly injected at a concentration of 0.1 ml/muscle into the muscles inside and outside the left and right femurs of 5-week-old female Balb/c mice (Orient Bio Co., Ltd., Korea). 100 μl of blood was collected from the infraorbital vein of the mice on the 3$^{rd}$ week, allowed to stand for about 20 minutes, and centrifuged at 10,000 rpm at 5±3° C. for 10 minutes, and then serum was obtained as a supernatant. The obtained serum was stored at −15° C. or lower.

TABLE 2

| Group | Composition of vaccine | Dosage (/100 μL) gE | Dosage (/100 μL) Al$^{3+}$ | The number of animals | Day of immunization | Day of bleeding | Day of sacrifice |
|---|---|---|---|---|---|---|---|
| 1 | Negative | X | X | 6 | wk 0 | wk 0 | |
| 2 | gE | 10 μg | X | 6 | | wk 3 | |
| 3 | gE + Alum | 10 μg | 5 mg | 6 | | | |
| 4 | gE + Alum | 10 μg | 1.25 mg | 6 | | | |
| 5 | gE + Alum | 10 μg | 1.0 mg | 6 | | | |
| 6 | gE + Alum | 10 μg | 0.5 mg | 6 | | | |
| 7 | gE + Alum | 10 μg | 0.2 mg | 6 | | | |
| 8 | gE + Alum | 10 μg | 0.1 mg | 6 | | | |
| 9 | gE + Alum | 10 μg | 0.05 mg | 6 | | | |
| 10 | gE + Alum | 10 μg | 0.025 mg | 6 | | | |
| | Total | | | 60 | | | |

Example 3: Ratio Optimization by Evaluation of Immunogenicity of Surface Protein (gE) and Alum In order to determine the optimal mixing ratio of antigen to alum in a vaccine composition containing a surface protein (gE) of Varicella zoster virus as an antigen, antibody formation reaction efficiency was determined from the serum obtained from Example 2 through the following ELISA method.

1. Plate Coating

The surface protein (gE) as the antigen was mixed with PBS (Lonza) at a concentration of 1 μg/mL, and the resulting mixture was dispensed at 100 μl/well into an ELISA immunoplate (Corning, USA) and was coated on the immunoplate at 5±3° C. overnight (over 16 hours) in the state in which the immunoplate was sealed with a plate sealer.

2. Blocking

After completion of the coating reaction, the solution on the plate was completely removed, and ELISA washing buffer which is PBS containing 0.05% Tween 20 was dispensed at 300 μl/well into each well using a multipipette. The plate was washed twice, 200 μl of PBS mixed with 2% BSA (Bovine serum albumin, Sigma) was added to each well, and the plate was sealed with a plate sealer and was allowed to react at room temperature (25±5° C.) for 1 hour. When blocking by BSA was completed, ELISA washing buffer was dispensed at 300 μl/well to each well using a multipipette and washing was performed twice. At this time, the plate was turned over and was strongly tapped (hit) on several pieces of paper towel in order to completely remove the solution in the plate during each washing.

3. Antigen-Antibody Response to Surface Protein (gE)

The mouse serum obtained and stored in Example 2 was diluted to 1:1000, 1:10,000, and 1:100,000 using ELISA assay buffer prepared by mixing 2% BSA with ELISA washing buffer, and the resulting serum was dispensed at 100 μl/well into each well, and was allowed to react at room temperature for 2 hours or longer in order to induce an antigen-antibody reaction. After the reaction was completed, the plate was turned over and was strongly tapped (hit) on several pieces of paper towel in order to completely remove the solution in the plate.

Then, the plate was washed with an ELISA washing buffer (300 μl per each well) 4 times using a multipipette, and the plate was turned over and was strongly tapped (hit)

on several pieces of paper towel in order to completely remove the solution in the plate during each washing.

4. 2$^{nd}$ Antibody Reaction and Absorbance Measurement

Goat anti-mouse IgG (H+L)-HRP (Southern Biotech), which was used as a secondary antibody, was prepared by diluting to 1:5,000 with ELISA assay buffer, and was dispensed at 100 μl/well to each well and was allowed to react at room temperature for 1 hour. After the reaction was completed, the plate was turned over and was strongly tapped (hit) on several pieces of paper towel in order to completely remove the solution in the plate. Then, each well was washed with ELISA washing buffer at 300 μl per well 5 times using a multipipette.

100 μl/well of TMB (3,3',5,5'-tetramethylbenzidine, KPL), which is a substrate of HRP, was added to the washed plate and was allowed to react at room temperature in the absence of light for 15 minutes. Then, 100 μL of a TMB stop solution (KPL) was added to each well to stop the enzymatic reaction and the absorbance was measured at 450 nm using an ELISA microplate reader (Spectramax 250, Molecular Device) to determine the amount of antibody produced.

As a result, it was found that, when the surface protein (gE) antigen was fixed at 5 μg and the aluminum concentration was changed, the highest immune response was induced in the case of adding 0.5 mg of an aluminum cation (FIG. 1).

In addition, it was found that, under different immunization conditions, when the surface protein (gE) was fixed at 10 μg and the aluminum concentration was changed, in the case of adding 1.0 mg of aluminum, that is, adjusting the ratio of antigen to aluminum cation to 1:100, the highest immune response was induced. In addition, it was found that, when the ratio of the antigen to the aluminum cation exceeded 1:100, the immune response was deteriorated (FIG. 2).

Example 4: Comparison in Immunity-Inducing Ability with Live Vaccine Against Varicella Zoster Virus The immunity-inducing ability was observed using a composition containing a mixture of a surface protein (gE) and an aluminum salt and the live attenuated Varicella Zoster Virus vaccine (Suduvax-Inj (Green Cross)) as follows.

1. Animal Immunization

5 μg of a surface protein (gE) alone; a mixture of 5 μg of a surface protein (gE) and 0.5 mg of an aluminum cation (Al$^{3+}$); and a live attenuated Varicella zoster virus vaccine (15000 PFU/0.5 mL) were prepared and subcutaneously or intramuscularly administered twice to Hartley guinea pigs at intervals of 3 weeks. PBS was used as a negative control. Three weeks after the last administration, blood was collected and the serum was separated.

TABLE 3

| Group | Composition of vaccine | Number of animals | Immunization | Bleeding |
|---|---|---|---|---|
| 1 | PBS | 3 | wk 0/wk 3 (im) | wk 6 (Cardiac Puncture) |
| 2 | 5 μg gE | 4 | | |
| 3 | 5 μg gE + 0.5 mg Al$^{3+}$ | 5 | | |
| 4 | Live vaccine (LAV, 15000 pfu/0.5 ml) | 4 | wk 0/wk 3 (SC) | | gP ELISA, Plaque Reduction Neutralization Test (PRNT), and Fluorescent-antibody-to-membrane-antigen (FAMA) test were conducted as follows to determine the titers of antibodies contained in the serum.

2. gP-Specific Antigen-Antibody Reaction (ELISA)

The VZV gP protein (VZV ELISA glycoprotein antigen; QED BIO, Cat No. BA104GVS) was dispensed at 0.1 μg per well into an ELISA plate and incubated at 4° C. overnight to coat the same with the protein antigen. A diluted serum sample was added to each well in the antigen-coated ELISA plate, incubated at room temperature for 2 hours, and washed with PBST. After completion of the antigen-antibody reaction, a HRP-conjugated rabbit anti-guinea-pig IgG antibody (Abcam, Cat No. ab6771) was added thereto, incubated again at room temperature for 1 hour and washed in the same manner as above. After washing, TMB was added as a substrate to induce color reaction by the enzyme bound to the secondary antibody. Finally, a stop solution was added to stop the reaction, and the optical density was measured at a wavelength of 450 nm using a spectroscope.

Figure 3:
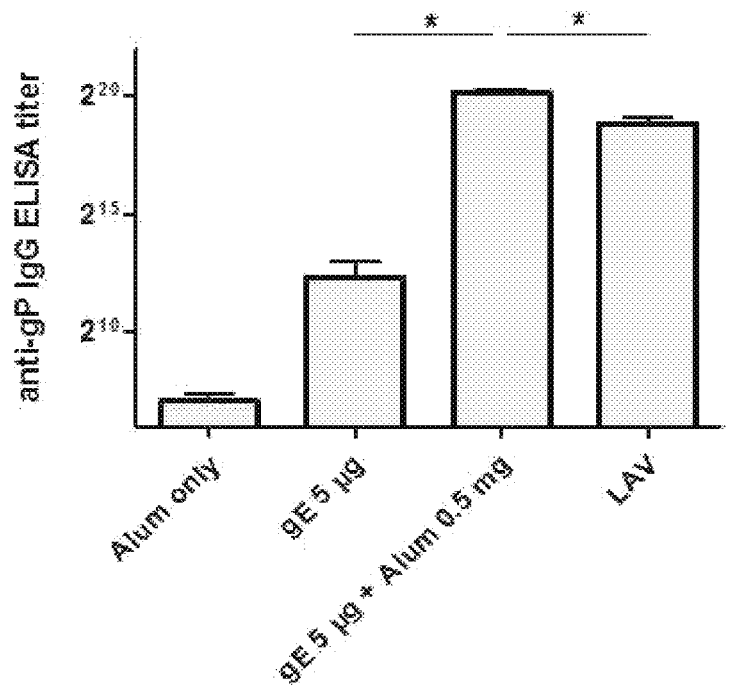
FIG. 3 is a graph showing ELISA results in order to determine antibody titers contained in serum after immunization with a surface protein (gE) and an aluminum salt for guinea pigs.

In conclusion, an anti-gP IgG ELISA assay was performed using an endpoint titration method in order to determine the increase of the VZV glycoprotein-specific antibody titer induced by immunization of the surface protein (gE) antigen. As a result, it was found that an antibody titer induced by a combination of 5 μg of gE and 0.5 mg of an aluminum cation (Al$^{3+}$) was significantly higher than that of a VZV gP-specific antibody titer induced by the live vaccine (about 15,000 PFU) (FIG. 3).

3. Plaque Reduction Neutralization Test (PRNT)

Whether or not a neutralizing antibody against VZV was induced by immunization of surface protein (gE) was identified by PRNT as follows.

The serum inactivated at 56° C. was serially diluted, mixed with the same volume of 1,000 PFU/ml of virus, and incubated at 37° C. for 1 hour. A 6-well plate prepared as a monolayer of MRC-5 cells (ECACC, Cat No. 05G007) was washed with PBS, the mixture of serum and virus was inoculated at 200 μl per well, after 1 hour and 30 minutes, a virus inoculation medium [MEM (Gibco Cat No. 11095-098)+2% FBS (Gibco, Cat No. 11360-070)] was added and incubated at 37° C. for 6 to 7 days, and stained with 0.5% crystal violet (Sigma, Cat No. C-3886), and the plaques were counted. The PRNT50 was determined by calculating the dilution rate showing a 50% neutralization ratio.

Figure 4:
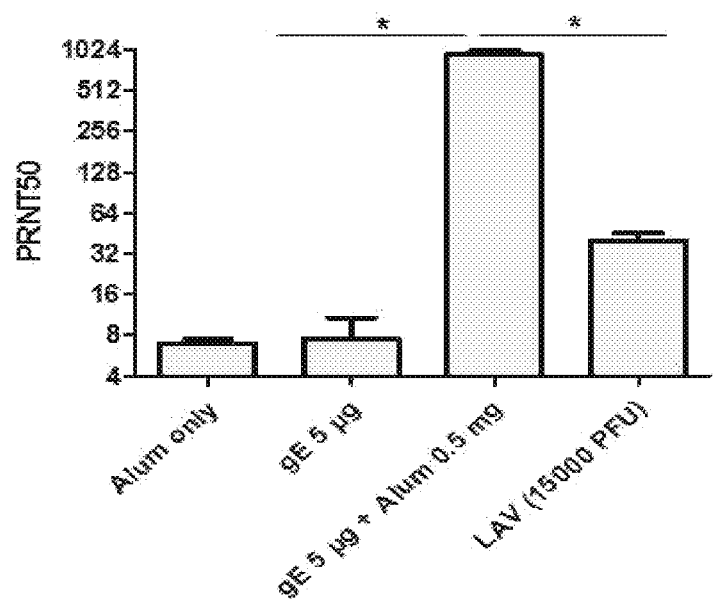
FIG. 4 is a graph showing analysis results of neutralizing antibody titers by a Plaque Reduction Neutralization Test (PRNT) in order to identify whether or not neutralizing antibodies against Varicella zoster virus are produced by immunization with a surface protein (gE) and an aluminum salt in guinea pigs.

As a result, it was found that the neutralizing antibody titer induced by the combination of 5 μg of gE and 0.5 mg of an aluminum cation (Al$^{3+}$) was significantly higher than that of the live vaccine (about 15,000 PFU) (FIG. 4).

4. Fluorescent-Antibody-to-Membrane-Antigen (FAMA) Test

Whether or not antibodies produced by gE immunization were able to bind to virus-infected cells was identified using FAMA, capable of identifying antibody titers of the virus-infected cells.

Cells infected with a VZV virus were prepared and 3×10$^5$ cells were added to serial-diluted serum and allowed to react for 30 minutes. After the reaction period, the infected cells were washed with PBS and reacted with Alexa-488-conjugated anti-guinea pig IgG (molecular probes, Cat No. D2650) for 20 minutes and washed again with PBS. Then, the cells were plated on a 14-well slide, dried, and examined using fluorescence microscopy. The cells stained by an Alexa488 fluorescent dye were observed in a field having 30 cells or more/field, and the final dilution rate at which fluorescence was observed was determined by FAMA titers.

Figure 5:
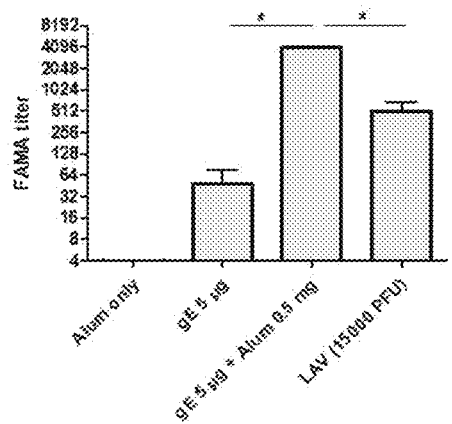
FIG. 5 is a graph showing whether or not antibodies, which are produced after administration of a surface protein (gE) and an aluminum salt to guinea pigs, can bind to cells infected with a Varicella zoster virus in order to determine antibody titers against virus-infected cells.

As a result, similar to the results of Anti-gP ELISA and PRNT50, the neutralizing antibody titer induced by the combination of 5 μg of gE and 0.5 mg of an aluminum cation (Al$^{3+}$) was found to be higher than that induced by the live vaccine (about 15000 PFU) (FIG. 5).

Example 5: Comparison in Immunity-Inducing Ability Depending on Type of Alum Salt The following experiment was conducted in order to determine the difference in immunity induction reaction depending on the kind of aluminum salt regarding the immunity induction effect of the Varicella zoster virus vaccine composition according to the present invention.

As shown in Table 4, 0.1 mL of mixtures of 0.1 mg based on the aluminum cation of various aluminum immune enhancer products and 5 μg of antigens (gE) were each intramuscularly administered to the left femur muscle of 5-week-old female Balb/c mice (Orient Bio Co., Korea). Details of the type of aluminum salt administered are given in Table 4 below.

TABLE 4

| Type of alum salt | Product name | Manufacturer | pH | Viscosity | Point of zero charge |
|---|---|---|---|---|---|
| Alhydrogel | Aluminum hydroxide | Alhydrogel | Invivogen | 7.8~8.0 | Gel-like | 10.5 |
| CT-HS | | Rehydragel HS | | 6.0~8.0 | 1300 cps max | 9.4 |
| CT-HPA | | REhydragel HPA | Chemtrade | 5.5~6.5 | Trixotropic | 12.1 |
| CT-LV | | Rehydraphos | | 5.8~6.8 | 1000 cps max | 11.6 |
| Al-Phos | Aluminum phosphate | | | 6.0~8.0 | Unknown | unknown |

100 μL of blood was collected from the infraorbital vein of mice at the 3$^{rd}$ week and was allowed to stand at room temperature for 20 minutes. Then, the blood was centrifuged at 10,000 rpm and at 5±3° C. for 10 minutes, and serum was obtained as a supernatant. The obtained serum was stored at −15° C. or less and the immunogenicity of the stored sample (serum) was identified by a gE ELISA method described in Example 3.

Figure 6:
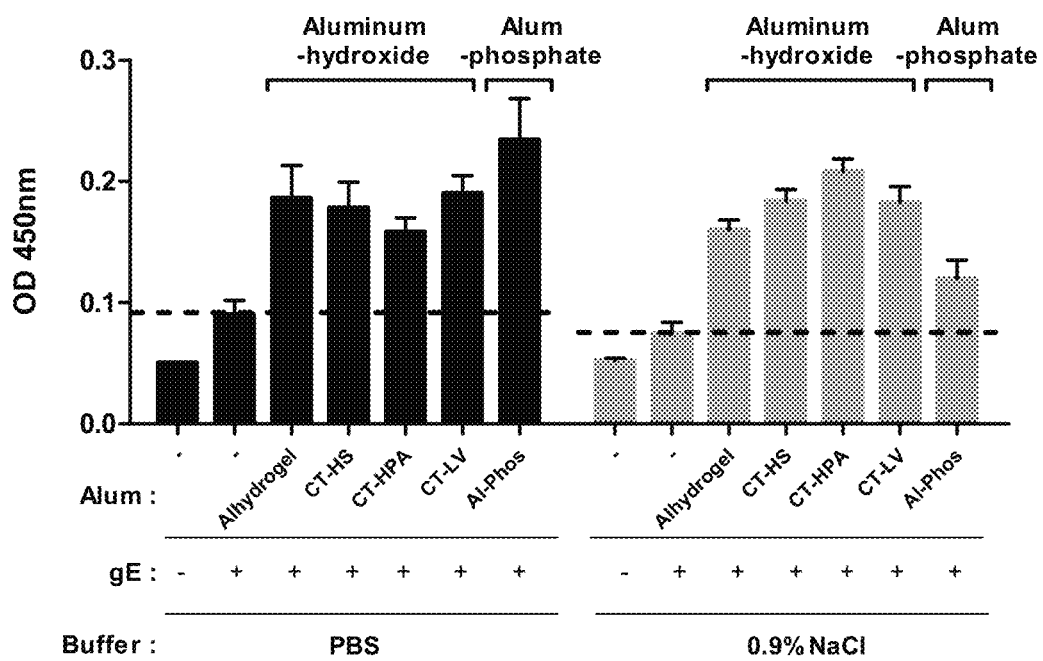
FIG. 6 is a graph showing the immunity-inducing ability of vaccine compositions containing different kinds of aluminum salts.

As a result, it was found that both aluminum hydroxide and aluminum phosphate induced higher immunogenicity than when an antigen was administered alone, although there was a slight difference depending on the product. In addition, it was found that the immunogenicity-inducing ability was superior to that of the antigen alone, regardless of whether the buffer of the preparation was changed to PBS and 0.9% NaCl (FIG. 6).

Although specific configurations of the present invention have been described in detail, those skilled in the art will appreciate that preferred embodiments of this description are given for illustrative purposes and should not be construed as limiting the scope of the present invention. Therefore, the substantial scope of the present invention is defined by the accompanying claims and equivalents thereto.

INDUSTRIAL AVAILABILITY

The vaccine composition according to the present invention is safer than a live bacterial vaccine since it uses protein antigens, and the vaccine composition can effectively exhibit an antibody-inducing ability since the mixing ratio of an immune enhancer (adjuvant) is optimized. Therefore, the vaccine composition is useful as a vaccine for preventing or treating varicella or herpes zoster induced by Varicella zoster virus.

SEQUENCE LISTING FREE TEXT

An electronic file is attached.

The invention claimed is:

1. A vaccine composition for preventing or treating varicella or herpes zoster comprising a surface protein gE of Varicella zoster virus having the amino acid sequence set forth in SEQ ID NO: 1 and an aluminum salt as active ingredients,
    wherein the content ration of the surface protein gE to aluminum cation ($Al^{3+}$) in the composition is 9:1000 to 22:1000 (weight ratio).

2. The vaccine composition according to claim 1, wherein the aluminum salt is aluminum hydroxide or aluminum phosphate.

3. The vaccine composition according to claim 1, further comprising at least one immune enhancer selected from the group consisting of calcium phosphate hydroxide, a mineral oil, squalene, an agonist of a toll-like receptor (TLR), a surfactant, liposome, saponin and cytokine.

4. The vaccine composition according to claim 2, wherein the content of aluminum in the composition is 0.2 to 5 mg.

5. The vaccine composition according to claim 1, wherein the content of the surface protein gE in the composition is 5 to 25 μg.

6. A method for preventing or treating varicella or herpes zoster comprising administering the vaccine composition according to claim 1 to a subject.

* * * * *

SEQUENCE LISTING

```
<160> NUMBER OF SEQ ID NOS: 1

<210> SEQ ID NO 1
<211> LENGTH: 537
<212> TYPE: PRT
<213> ORGANISM: Artificial Sequence
<220> FEATURE:
<223> OTHER INFORMATION: gE of Varicella Zoster Virus
```

<400> SEQUENCE: 1

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Cys Leu Tyr His Pro
385                 390                 395                 400

Asn Ala Pro Gln Cys Leu Ser His Met Asn Ser Gly Cys Thr Phe Thr
                405                 410                 415
```

```
Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg
530                 535
```